United States Patent [19]
Lisa et al.

[11] Patent Number: 5,593,948
[45] Date of Patent: Jan. 14, 1997

[54] HIGHLY CONCENTRATED, SOLID ACIFLUOREN POWDERS AND PROCESSES FOR MAKING DRY FORM SOLID ACIFLUORFEN POWDERS

[75] Inventors: Rudolph E. Lisa, Grosse Ile; Terence K. Kilbride, Jr., Bloomfield Hills, both of Mich.

[73] Assignee: BASF Corporation, Mount Olive, N.J.

[21] Appl. No.: 234,886

[22] Filed: Apr. 28, 1994

[51] Int. Cl.$^6$ .......................... A01N 25/14; A01N 37/10
[52] U.S. Cl. .......................... 504/324; 71/DIG. 1
[58] Field of Search .......................... 504/324; 71/DIG. 1

[56] References Cited

U.S. PATENT DOCUMENTS

| | | | |
|---|---|---|---|
| 4,936,901 | 6/1990 | Surgant, Sr. et al. | 71/92 |
| 4,946,654 | 8/1990 | Uhlemann et al. | 422/140 |
| 5,026,895 | 6/1991 | Bakos et al. | 560/21 |
| 5,372,989 | 12/1994 | Geigle et al. | 504/116 |
| 5,380,350 | 1/1995 | Fersch | 71/64.03 |

*Primary Examiner*—S. Mark Clardy
*Attorney, Agent, or Firm*—Joanne P. Will

[57] ABSTRACT

The present invention provides hygroscopic herbicide formulations in dry, flowable powder forms and associated methods of making the powders and tablets. The most preferred formulation uses an effective amount of a acifluorfen combined with a citrate sequestrant.

22 Claims, 3 Drawing Sheets

HIGHLY CONCENTRATED, SOLID ACIFLUOREN POWDERS AND PROCESSES FOR MAKING DRY FORM SOLID ACIFLUORFEN POWDERS

BACKGROUND OF THE INVENTION

1. Field of Invention

The present invention relates to methods for making flowable, highly concentrated dry acifluorfen powders from an aqueous solution of the salt form of acifluorfen.

2. Background of the Prior Art

Herbicides may be applied to plants in a variety of methods including different formulations. Of these various methods, use of liquid and dry compositions are the most common. The particular formulation desired and resulting efficacy enhancement will greatly depend upon the species to be treated, environmental conditions, the geographical area and the climatology of the area at the time of treatment.

The herbicide, known trivially as acifluorfen, is widely used to control various weeds, such as morning glory, pigweed, ragweed, velvetleaf, foxtail, johnson grass, Florida beggarweed, cocklebur, and others. See, for example, U.S. Pat. Nos. 3,798,276 and 3,928,416.

Further patents claim enhanced herbicidal activity for acifluorfen and its agronomically acceptable salt forms with the addition of one water-soluble salt from an organic or inorganic acid (see, U.S. Pat. No. 4,508,559), and specifically by the addition of a citrate salt (see, U.S. Pat. No. 4,549,903).

Acifluorfen's chemical name is 5-(2-chloro-4-(trifluoromethyl)phenoxy)-2-nitrobenzoic acid and is available from BASF Corporation under the trademarks BLAZER® or TACKLE®. These products are manufactured in the form of about a 43 to 48% active ingredient aqueous solution of the sodium acifluorfen with impurities (This product is sold by BASF Corporation under the trademark BLAZER® TECHNICAL).

The end user normally purchases acifluorfen either as an aqueous mixture of sodium acifluorfen, trisodium citrate, and a co-solvent butyl cellosolve (BLAZER®); or as sodium acifluorfen, a sodium lignin sulfonate—REAX 910 (from Westvaco Corporation), and co-solvent propylene glycol (TACKLE®).

Acifluorfen is preferentially sold in agronomically acceptable salt forms mentioned above because the salt form has a high water solubility which imparts convenience to the farmer who applies the product from this tractor tank. The sodium form, for example, has a water solubility of more than 119 g/L. The aqueous solution can be added directly to an application tank containing water, recirculated for a few minutes, and applied as a dilute aqueous liquid to the plant growth in the fields.

The acifluorfen in its acid form is not soluble in water to any appreciable extent, and presents dispersion problems using an application tank to apply the chemical universally in the field.

Until now, the high water solubility of the salt forms have given it an advantage over the water insoluble acid form for the end user. However, the high hygroscopicity of the salt form makes it difficult to dry the salt form. The water is difficult to remove during drying.

Attempts to remove the water from acifluorfen formulations by spray drying have resulted in a sticky, non-flowable mass, most of which stuck to the walls, ducts, and cyclone walls of the spray dryer, rendering the process ineffective.

Similarly, attempts to dry acifluorfen formulations, such as solutions of REAX 910 with BLAZER®, by use of a double drum dryer resulted in the formation of a sticky material that could not be scraped off the drums.

Furthermore, drying generally is also hindered by foaming which can result in certain dryers being ineffective. In batch drying for example, foaming can greatly hinder the rate of drying, or even eliminate the possibility of drying such a compound sufficiently to form a powder. All three commercial formulations of acifluorfen, (BLAZER® Technical, BLAZER®, and TACKLE®) could not be dried in several batch driers. Attempts to dry these products in either a rotary dryer or a mechanical fluid bed dryer with chopping blades (for example, the Littleford FKM dryer) resulted in violent foaming, which rendered the process ineffective.

Generally, solid forms of herbicides offer a number of key advantages, including convenience, increased stability and shelf life, as well as reduced packaging, storage and shipping costs. Additionally, there is the possibility of future government regulation requiring solid forms of agricultural products in order to reduce handling of contaminated packaging of these products during field application and during disposal. These dry flowable hygroscopic herbicidal compounds would be safer for the farmer to use and dispose of, and also result in a smaller volume of hazardous waste being produced. If the dry herbicide can be filled into dissolvable bags which are added to the tractor tank, then exposure during loading and the hazardous waste generated can be virtually eliminated.

There is a need for a dry, flowable, highly concentrated powder form of hygroscopic acifluorfen suitable for filling water dissolvable bags. The ideal dry powder would not only include the active ingredient, but also a sequestering agent such as a citrate salt.

SUMMARY OF INVENTION

Surprisingly, a free-flowing, non-caking solid salt form acifluorfen (such as sodium acifluorfen) containing a citrate salt sequesterant can be produced by spray drying such a solution. The citrate salt is dissolved in acifluorfen (BLAZER® TECHNICAL) solution, and the resulting solution spray dried to form a free flowing, dry powder, with about 73% active sodium acifluorfen.

Optionally, suitable inerts such as silica can be added to the spray tower as anti-caking agents. Additionally, a dry powder acifluorfen with citrate salt can also be produced on a drum dryer.

The preferred forms of acifluorfen of the present invention include all agronomically acceptable salts of the acifluorfen, most preferably sodium acifluorfen.

It is an object of the present invention to provide an agriculturally acceptable acifluorfen formulation in a solid form.

It is an object of the present invention to provide a dry, flowable powder form of acifluorfen suitable for filling into and use in water soluble bags.

It is an object of the present invention to provide a spray drying process to produce an acifluorfen dry powder.

It is an object of this invention to provide a drum drying process to produce an acifluorfen dry powder.

DETAILED DESCRIPTION OF THE PREFERRED EMBODIMENTS

As used herein, the term "agriculturally acceptable" includes the present agricultural, industrial and residential use.

As used herein, acifluorfen formulations of the present invention may be used to form both package and tank mix compositions.

The present preferred invention comprises herbicide compositions comprising an agriculturally and plant growth regulating effective amount of acifluorfen, or any of its herbicidally effective derivatives or salts, in a dry flowable highly concentrated powder. The most preferred acifluorfen form is sodium acifluorfen. This product is commercially available under the registered trademark BLAZER® (BASF Corporation).

For convenience of description, sodium acifluorfen will be used as an example. However, the methods described apply equally to other salt forms of acifluorfen. Similarly, sequestrants such as sodium citrate will be used in the examples, although other sequestrants and citrate forms are equally applicable. In general it is preferred that the weight of a sequestrant, such as a citrate salt, per weight of acifluorfen is about 0.1:100 to about 35:1.

While the ratios of the concentrations of the various components of the present invention hereinafter suggested, those skilled in the art will recognize that minor variations may be necessary to accommodate particular characteristics of acceptable formulations of the various salt forms of acifluorfen which may be employed in this invention.

Figure 1:
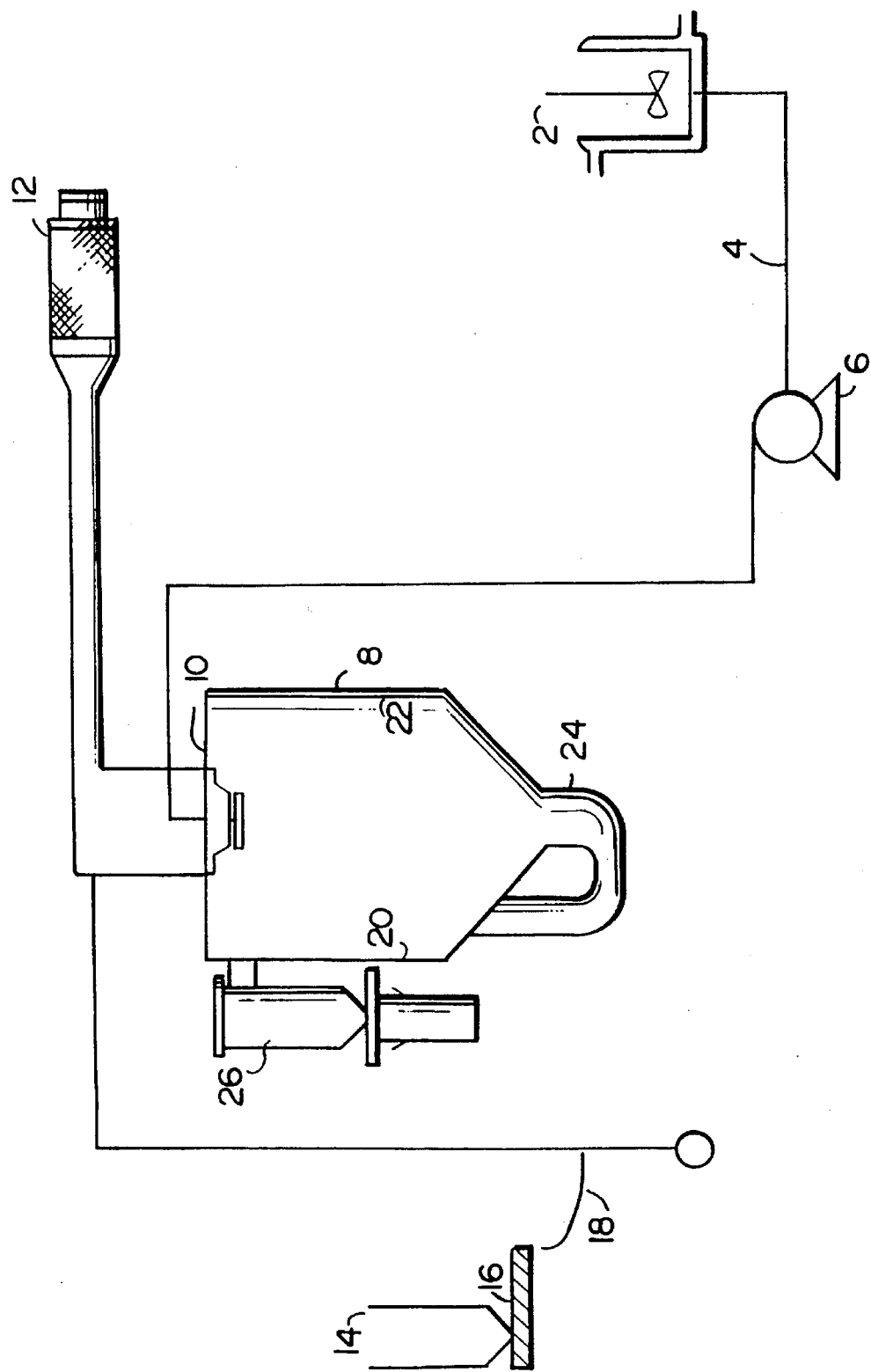
FIG. 1 illustrates a spray dryer used in a method of the present invention.

A preferred embodiment of the present invention consists of a spray dryer of the type illustrated in FIG. 1 may be used. As can be shown from FIG. 1, a sequestrant, tri-sodium citrate is combined in the sodium acifluorfen aqueous solution in an agitated feed tank (2) and fed through a line (4) via a feed pump (6) into the spray dryer unit (8). The aqueous acifluorfen feed solution is introduced into the spray dryer unit (8) by an atomizing means (10). An inlet air heating means (12) provides heat to the dryer at a temperature of about 150° to about 250° C. The formed droplets are heated by the hot air, and the water in the droplet is evaporated, forming a solid particle containing the acifluorfen salt and the sequesterant. The dry particles are swept into the air stream to the exit duct (24) and finally to the cyclone (26) where the particles are separated from the air by centrifugal action. The collection system may also include a bag filter to recover the solid particles.

A flow aid, such as silica, may optionally be stored in a feed hopper (14) and injected into the spray dryer unit (8) via a screw feeder (16) through a line by an air eductor (18). Alternatively, the flow aid can be introduced in the heating duct or top of the chamber at a point of negative pressure. The flow aide adheres to the forming droplets or partially dried particles and reduces the tendency of the partially dry particles to stick on the walls of the drying chamber. Furthermore, the flow aid also aids the product in storage by reducing the tendency to cake or lump, particularly when exposed to atmospheric moisture.

It is preferred that the sodium acifluorfen solution be initially heated to about 60° C. before adding the sequestrant. This greatly reduces the tendency of the acifluorfen solution to foam on addition of the sequestrant.

The rate at which the aqueous acifluorfen feed solution is fed into the spray dryer is not critical and is dependent upon the size of the spray dryer used. This rate is easily determined by those skilled in the art.

Figure 2:
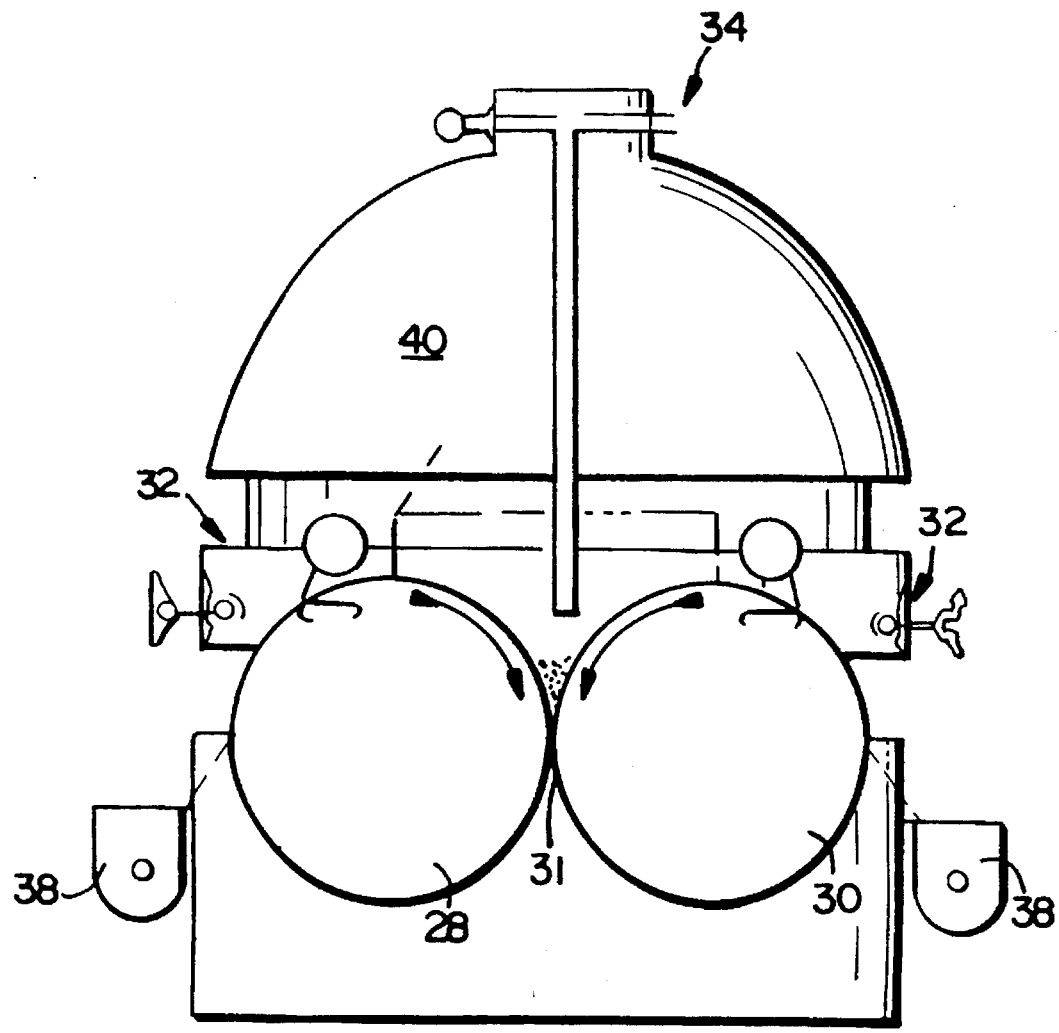
FIG. 2 illustrates a double drum dryer used in a method of the present invention.

A preferred method dries the acifluorfen/sequestrant solution with a double drum dryer as illustrated in FIG. 2. The double drum dryer has a pair of hollow, rotating drums (28, 30) whose surfaces are scraped by a knife (32). High pressure steam is introduced to the interior of the drums and acifluorfen solution added continuously via a feed line (34) to the nip between the drums (36). The acifluorfen solution must be prepared by adding sequestrant to an agitated tank, as in the spray drying example.

The drums turn toward one another, by means of a conveyor (38) depositing a portion of the liquid, boiling acifluorfen solution on the drum surface (28, 30) where boiling is initiated. Upon further rotation, the thin film of acifluorfen's water boils off into the vapor hood (40) and a solid film remains that is scraped by sharp knifes (32) from the turning drum surfaces (28, 30). The material is then collected and optionally, a flow aid may be added to improve flowability and impart anti-caking properties prior to filling water soluble bags. Optionally, the flakes from this process may be ground to improve flowability.

Both processes optionally use silica or other flow aids to reduce caking in the drum or water soluble bag, and to reduce adherence to equipment. Other inert additives include any form of silica including fumed silicas, precipitated silicas, aluminum silicates, magnesium silicates, and the like, zeolites, bentoinites, montmorillonites, and attapulgites, and mixtures thereof.

The preferred silica is known commercially as Sipernat® 50S. The weight of the optional silica per weight of the herbicide formula in all these drying processes is about 0.2:100 to about 3:100, and more preferably about 2:100. This ratio is based on the overall formula, not just the active ingredient.

Optionally, to further improve flowability, reduce sticking tendency or caking, or to increase the dissolution rate, binders, fillers, and/or disintegrants can be dissolved in the feed solution before drying. Suitable binders, fillers, and/or disintegrants include water-soluble cellulose derivatives, cellulose derivatives, carboxymethyl cellulose, hydroxypropyl methylcellulose, water soluble gums such as gum arabic, gum tragacanth, alginates, gelatin, and polyvinylpyrrolidone, cross-linked polyvinyl-pyrollidone, microcrystalline cellulose, modified starches such as sodium carboxymethyl starch, and mixtures thereof.

Other suitable fillers, binders, and/or disintegrants include any water soluble starch, corn syrup, dextrin or pregelatinized starch which is at least partially soluble in water at ambient temperature. For example, there can be used as a binder the pregelatinized, modified and stabilized waxy maize starch (commercially available from National Starch and Chemical Corporation under the trade name Instant Celar Gel). In addition, pregelatinized corn starch (commercially available from Hubinger Company under the trade name OK Pre-Gel) may be used.

Other binders suitable for use are pregelatinized food starch, refined from tapioca and marketed under the trade name Instant Gel; stable, modified amylopectin marketed under the trade name Kosol; a low viscosity tapioca dextrin marketed under the trade name Crystal Gum; dextrinized corn starch marketed under the trade name Purity Glaze;

maltodextrin marketed under the trade name Maltrin, such as M040 by Grain Processing Corporation.

It is preferred that the binders, fillers, and disintegrants be present in an amount of about 0.1 to about 99.7%.

All of the above-described powders, with and without fillers, binders, and/or disintegrating agents can then be filled in water soluble bags.

In general the formulations of the present invention contain from about 0.1 to about 80% active ingredient, and preferably from about 40 to about 70% active sodium acifluorfen. Typically, for the herbicide concentrate of the present invention, the concentration of regulator active ingredient (based on sodium acifluorfen) is about 65 to about 500 gms/acre.

In addition to the above-described components, the compositions of the present invention may also include other ingredients or adjuvants commonly employed in the art.

Examples of such ingredients include drift control agents, defoaming agents, preservatives, surfactants, fertilizers, phytotoxicants, plant growth regulators, pesticides, insecticides, fungicides, wetting agents, adherents, nematocides, bactericides, trace elements, synergists, antidotes, mixtures thereof and other such adjuvants well known in the herbicidal art.

However, it is preferred to employ the compositions of the present invention along with sequential treatments with these other components for optimal effect.

The compositions of the present invention may be applied to plants. The application of liquid and particulate solid herbicide compositions to above ground portions of plants may be carried out by conventional methods, for example, boom and hand application, including sprayers or dusters. The composition may be applied aerially as a spray, if desired. The mixtures of the present invention are preferably used in the form of aqueous solutions. The mixtures are applied in a conventional manner, for example, by spraying, atomizing, watering or disinfecting seed.

The forms of application depend entirely on the purpose for which the compositions are being used. In any event, they should ensure a fine distribution of the active ingredients in the composition. The above herbicide formulations may then be dispersed in water and sprayed onto plants according to the method of the present invention.

Powders, dusts and broadcasting agents may be prepared by mixing or grinding the active ingredients with a solid carrier.

Granules, for example, coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics fertilizers such as ammonium sulfate, ammonium phosphate, ammonium nitrate, and ureas, and vegetable products such as grain flours, bark meal, wood meal, and nutshell meal, cellulosic powders, and the like.

The action of the compositions of the present invention are optimal even at low application rates. For a given herbicide composition, the skilled artisan will readily arrive at a composition having the optimum ratio of the ingredients by routine experimentation.

The compositions of this invention may be prepared, for example, by adding, in any order, the various components of the composition of the present invention. For example, one may start with a commercial formulation of acifluorfen, which is an aqueous concentrate containing about 43 to about 48% active sodium acifluorfen. Thereafter, in any order, one mixes suitable amounts of any optional adjuvants or ingredients.

The following examples serve to illustrate the invention and should in no way be construed as limiting the scope thereof.

EXAMPLES

Example 1

12,884 grams of a sodium acifluorfen solution (BLAZER® Technical) of 44.76% active sodium acifluorfen was added to an agitated jacketed spray dryer feed tank and heated to 66° C. with tempered water. To this solution was added 2,116 g of trisodium citrate (moisture content 14%) and mixed until the citrate was dissolved. The resulting solution had a viscosity of 110 centipoise at 66° C. This solution was pumped at 111 to 128 g/min. to a 5 inch slotted atomizing wheel rotating at about 17,000 rpm in a Niro Utility spray dryer. The droplets formed by this method were dried by 175° C. inlet air, with a resulting outlet temperature of about 117° to about 126° C.

The resultant powder was collected in a cyclone separator. The powder was flowable and produced minimal wall deposits. Analysis of the powder showed that the powder had 0.99% moisture, untapped bulk density of 0.41 g/cc, a tapped bulk density of 0.52 g/cc. The ash content was measured at 7.15%. This demonstrates that a flowable dry powder of normal bulk density and moisture content for a spray dried powder was produced. The powder was suitable for filling water soluble bags.

Example 2

The experiment of Example 1 was repeated, but Sipernat 50S silica from a loss-in-weight screw feeder was injected via an air eductor into the air plenum to mix with the heated air entering the drying chamber. The silica was fed at a rate of 3%, based on the dry basis feed rate of the acifluorfen feed solution. The silica/air mixture was maintained at 175° C., then the mixture entered the drying chamber, intermixing with the droplets formed by the atomizer. The resultant outlet temperature was about 109° to 125° C.

On drying, the powder exited the drying chamber and was separated by a cyclone separator. The powder was flowable and produced minimal wall deposits. Analysis of the powder showed that the powder had 0.50% moisture, a bulk density of 0.42 gm/cc untapped, and 0.53 g/cc tapped, with an ash content of 8.10%. This ash content implies a silica content, as compared to Example 1, of 0.95%. This powder was also suitable for filling water soluble bags.

Example 3

A hot solution of 5000 gms of BLAZER® Technical liquid with 835 gms of trisodium citrate was prepared as in Example 1. The solution was dripped onto the rolls between the nip of a lab scale double drum dryer, with the hot rolls rotating at about 6 rpm. The rolls were heated with 80 psig steam. The material adhered to the rolls and the moisture evaporated while the drums rotated. The solid film was scraped off the rolls by blades and collected. The resulting sheets of dried solid broke easily into a granular, flowable powder with a bulk density of 0.39 gm/cc untapped, 0.56 gm/cc tapped, and moisture of 1.0%. These results were judged acceptable for filling water soluble bags.

Example 4

A greenhouse trial was conducted to assess the weed killing efficacy and crop injury potential of various surfactants and acifluorfen, compared with two intermediate dry, flowable formulations of acifluorfen and trisodium citrate (Examples 1 and 2). The two formulas of Examples 1 and 2 demonstrated weed efficacy and crop phytotoxicity similar to the control formula. The results in this test showed that the dry flowable formulations of Examples 1 and 2 worked as well as the other control formulas.

In contrast to the above examples, the following Examples illustrate the difficulty of drying acifluorfen formulations.

Example 5

A solution of 5000 gms of BLAZER® Technical liquid with 81 grams of Reax 910 was prepared (simulating the TACKLE® formula) in the same equipment used to prepare the feed solution of Example 1. The spray dryer again was operated at 175° C. inlet temperature, and the atomizing wheel revolved at 17,000 rpm and the feed added as in Example 1. The resultant powder was an extremely fine, sticky dust the bulk of which adhered to the walls of the spray dryer. The powder which was recovered would not flow, and because of this was not suitable for filling water soluble bags.

Example 6

BLAZER® Technical liquid was heated to 60° C. and dripped on the nips of the double drum dryer rolls at the conditions of Example 3. Even when the rolls were slowed down, the material was too gummy to be flaked with the blades. It was concluded that a flowable powder could not be formed by this method.

Example 7

A solution of BLAZER® Technical and Reax 910 was prepared in the method of Example 5. The 60° C. liquid was dripped on the nip of the double drum dryer rolls at the conditions of Example 3. Even when the rolls slowed down, the material was too gummy to be flaked with the blades. It was concluded that a flowable powder could not be formed by this method.

Example 8

Figure 3:
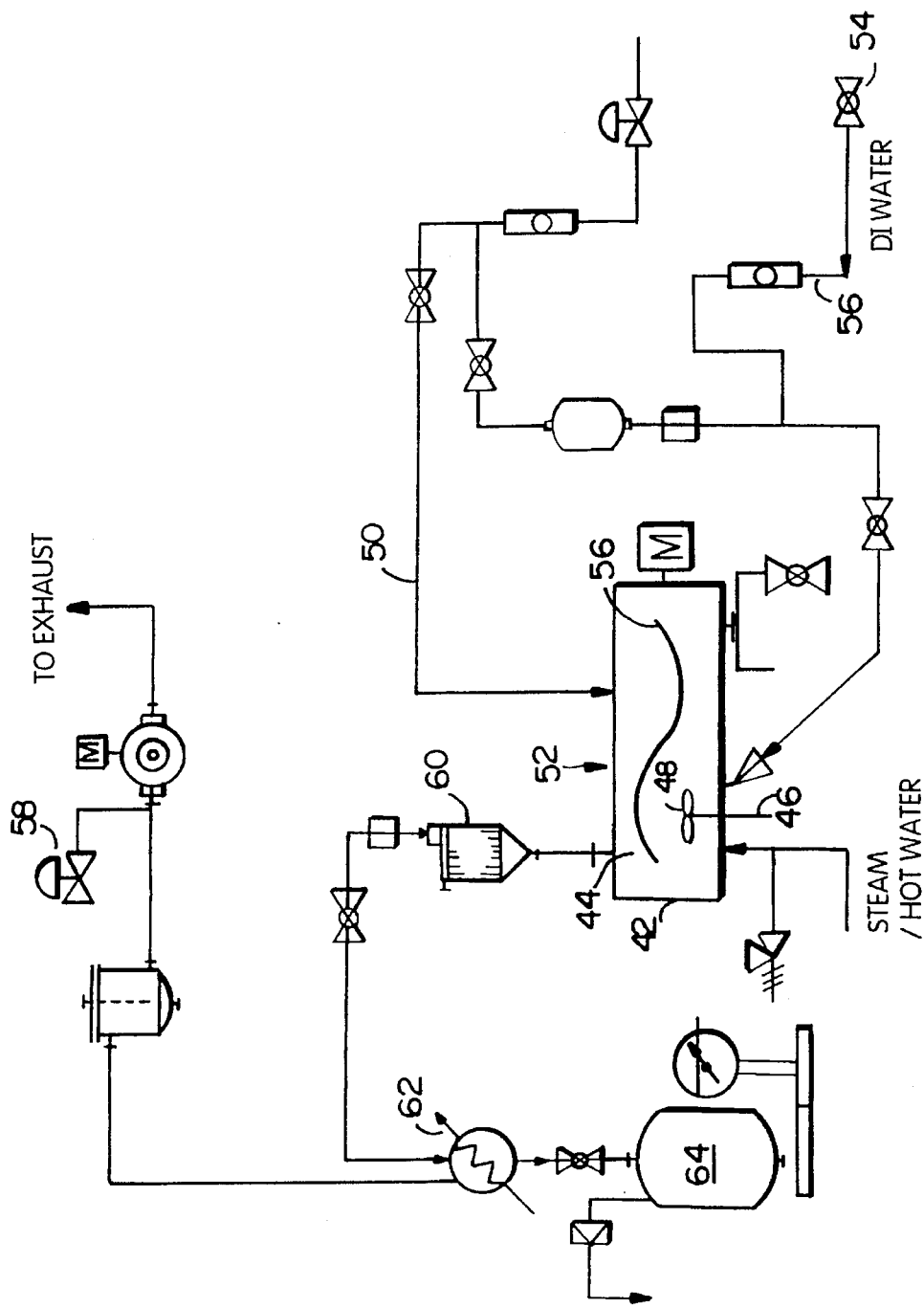
FIG. 3 illustrates a Littleford vacuum dryer used in Examples 8–10.

Another method of drying the acifluorfen was made using a batch vacuum dryer with chopping blades, described as a "mechanical fluidized bed", a typical example of which is the Littleford type (or Lodige) vacuum dryer, as shown in FIG. 3.

This unit consists of a double jacket (2, 4). Inside the double jacket is a hollow rotating shaft (6) with attached plough shaped mixing elements (8). A high shear chopping assembly extends into the product cavity through the wall via a flange mounting (10).

This type of unit is commonly employed by those skilled in the art to evaporate a solution to dryness, using the chopping blade to chop up the pasty material that forms as the moisture is lost. By virtue of heat from the jacket, and vacuum supplied to the unit, moisture is evaporated. The chopping blade breaks up the large, pasty particles so that fresh surface laden with moisture to be evaporated is continuously exposed so that drying rate is increased.

The feed solutions of the composition of Example 1, Example 5, and Example 6 were fed to a 130 liter Littleford dryer (Model FKM-130 with chopping blade). 171 lbs of trisodium citrate/sodium acifluorfen solution of the formula in Example 1 was charged to the Littleford and heat-up begun, running the plough agitator at 80 rpm. No appreciable moisture was removed between 60° and 100° C. with vacuums of 160 mm Hg absolute in the vessel. As it approached 100° C. the solution foamed violently, and the foaming could not be controlled.

Example 9

An experiment similar to Example 8, using a solution of 153 lbs of Reax 910/sodium acifluorfen was attempted using the Littleford dryer. At 80 rpm, and 60°–70° C. in the dryer, moisture could be slowly removed, but when the pasty state was reached, moisture could no longer be evaporated, even with the chopping blade running, 50 mm Hg absolute vacuum, and at temperatures exceeding 120° C. An examination of the interior of the dryer indicated that the material was in one large lump, and had to be chipped out.

Example 10

An experiment was attempted using the feed of Example 7, BLAZER® Technical. 150 lbs of this liquid was charged and heat-up begun. A vacuum of 460 mm Hg was pulled. Even at temperatures below 60° C., the batch foamed badly, and moisture could not be removed to any appreciable extent.

Examples 8–10 illustrate the disadvantages of using a Littleford vacuum dryer as a means to dry these materials to a flowable powder.

Whereas particular embodiments of the invention have been described above for purposes of illustration, it will be appreciated by those skilled in the art that numerous variations of the details may be made without departing form the invention as described in the appended claims.

What is claimed is:

1. A method of making a dry, flowable powder of acifluorfen or its agronomically acceptable salts using a spray dryer comprising dissolving a citrate sequestrant in an aqueous solution of acifluorfen salt at an elevated temperature and drying said acifluorfen.

2. A method of claim 1, wherein the acifluorfen form is sodium acifluorfen.

3. A method of claim 1, wherein the citrate is selected from a group consisting of sodium citrates, ammonium citrates, and potassium citrates.

4. A method of claim 3, wherein the citrate is tri-sodium citrate.

5. A method of claim 1, wherein an effective amount of inert is added to the aqueous solution of acifluorfen.

6. The method of claim 1, wherein said inerts are dispersed in the aqueous acifluorfen feed solution before drying.

7. A method of claim 1 wherein the weight of citrate salt per weight of acifluorfen is about 0.1:100 to about 35:1.

8. A method of claim 7 wherein the inert is selected from a group consisting of silicas, fumed silicas, precipitated silicas, aluminum silicates, magnesium silicates, zeolites, bentonites, montmorillonites, attapulgites, and mixtures thereof.

9. A method of claim 8 wherein the weight of inert per weight of acifluorfen used is about 0.2:100 to about 3.0:100.

10. A method of claim 1 wherein the dry flowable powder comprises fillers, binders or disintegrants.

11. A method of claim 10, wherein the fillers, binders, or disintegrants are selected from the group consisting of water soluble cellulose derivatives, cellulose derivatives, carboxymethyl cellulose, hydroxypropyl methylcellulose, water soluble plant gums, alginates, gelatin, polyvinylpyrrolidone, water soluble starch, corn syrup, dextrin, pregelatinized starch which is at least partially soluble in water at ambient temperature, pregelatinized food starch, stable, modified amylopectin, a low viscosity tapioca dextrin, dextrinized corn starch, maltodextrin, microcrystalline cellulose, crosslinked polyvinyl pyrollidone, sodium carboxymethyl starch, and mixtures thereof.

12. A method of claim 10 wherein the binders, fillers, or disintegrants are dissolved in the acifluorfen solution before drying.

13. A method of claim 10 wherein the binders, fillers, and disintegrants are present in an amount of about 0.1 to about 99.7%.

14. A method of making a dry, flowable powder of acifluorfen using a spray dryer comprising:

injecting aqueous acifluorfen feed solution containing tri-sodium citrate into said spray dryer at a controlled rate; and injecting an inert in the inlet air stream of said spray dryer at a controlled rate, whereby the inert adheres to droplets of said acifluorfen forming a dry, flowable powder.

15. A method of claim 14, wherein the inert is selected from a group consisting of silicas, fumed silicas, precipitated silicas, aluminum silicates, magnesium silicates, zeolites, bentonites, montmorillonites, attapulgites, and mixtures thereof.

16. A method of claim 14, wherein the weight of inert per weight of acifluorfen used is about 0.2:100 to 3.0:100.

17. A method of claim 14, wherein said inerts are dispersed in the aqueous acifluorfen feed solution before drying.

18. A method of claim 14 wherein the dry flowable powder comprises fillers, binders, and/or disintegrants.

19. A method of claim 18, wherein the fillers, binders, and/or disintegrants are selected from the group consisting of water soluble cellulose derivatives, cellulose derivatives, carboxymethyl cellulose, hydroxypropyl methylcellulose, water soluble plant gums, alginates, gelatin, polyvinylpyrrolidone, water soluble starch, corn syrup, dextrin, pregelatinized starch which is at least partially soluble in water at ambient temperature, pregelatinized food starch, stable, modified amylopectin, a low viscosity tapioca dextrin, dextrinized corn starch, maltodextrin, microcrystalline cellulose, crosslinked polyvinyl pyrollidone, sodium carboxymethyl starch, and mixtures thereof.

20. The method of claim 14, wherein the binders, fillers, and disintegrants are dissolved in the acifluorfen solution before drying.

21. The method of claim 14, wherein the binders, fillers, and disintegrants are present in an amount of about 0.1 to about 99.7%.

22. The method of claim 14, wherein the acifluorfen is present as a sodium salt.

* * * * *